United States Patent
Delpy et al.

(10) Patent No.: US 10,398,722 B2
(45) Date of Patent: Sep. 3, 2019

(54) USE OF ANTISENSE OLIGONUCLEOTIDES FOR PRODUCING TRUNCATED IG BY EXON SKIPPING FOR THE TREATMENT OF DISEASES INVOLVING B CELLS

(71) Applicants: Universite de Limoges, Limoges (FR); Centre National de la Recherche Scientifique, Paris (FR)

(72) Inventors: Laurent Delpy, Limoges (FR); Nivine Srour, Limoges (FR); Michel Cogné, Limoges (FR)

(73) Assignees: Universite de Limoges, Limoges (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 15/777,843

(22) PCT Filed: Nov. 22, 2016

(86) PCT No.: PCT/EP2016/078475
§ 371 (c)(1),
(2) Date: May 21, 2018

(87) PCT Pub. No.: WO2017/089359
PCT Pub. Date: Jun. 1, 2017

(65) Prior Publication Data
US 2018/0344760 A1    Dec. 6, 2018

(30) Foreign Application Priority Data

Nov. 23, 2015  (FR) .................................... 15 61252

(51) Int. Cl.
*A61K 31/713* (2006.01)
*C12N 15/113* (2010.01)
*A61K 45/06* (2006.01)
*A61P 35/04* (2006.01)

(52) U.S. Cl.
CPC ............ *A61K 31/713* (2013.01); *A61K 45/06* (2013.01); *A61P 35/04* (2018.01); *C12N 15/113* (2013.01)

(58) Field of Classification Search
None
See application file for complete search history.

(56) References Cited

PUBLICATIONS

Hall et al., "Specific Inhibition of IgE Antibody Production by an Antisense Oligodeoxynucleotide Oligomer (Oligostick)," Immunology, 77: 462-464 (1992).
Cogné et al., "Exon skipping without splice site mutation accounting for abnormal immunoglobulin chains in nonsecretory human myeloma," European Journal of Immunology, 23: 1289-1293 (1993).
Meister et al., "Extensive immunoglobulin production sensitizes myeloma cells for proteasome inhibition," Cancer Research, 67: 1783-1792 (2007).
Srour et al., "A plasma cell differentiation quality control ablates B cell clones with biallelic Ig rearrangements and truncated Ig production," Journal of Experimental Medicine, 213: 109-122 (2016).
International Search Report issued in corresponding International Patent Application No. PCT/EP2016/078475 dated Mar. 6, 2017.

*Primary Examiner* — Tracy Vivlemore
(74) *Attorney, Agent, or Firm* — Morgan, Lewis & Bockius LLP

(57) ABSTRACT

The present invention concerns a treatment of diseases involving B cells, B lymphocytes or plasmocytes. In particular, it concerns an antisense oligonucleotide or a mixture of antisense oligonucleotides capable of inducing exon skipping at the RNA of the immunoglobulin heavy or light chains, for the use of same in the treatment of diseases involving B cells.

Figure 1:
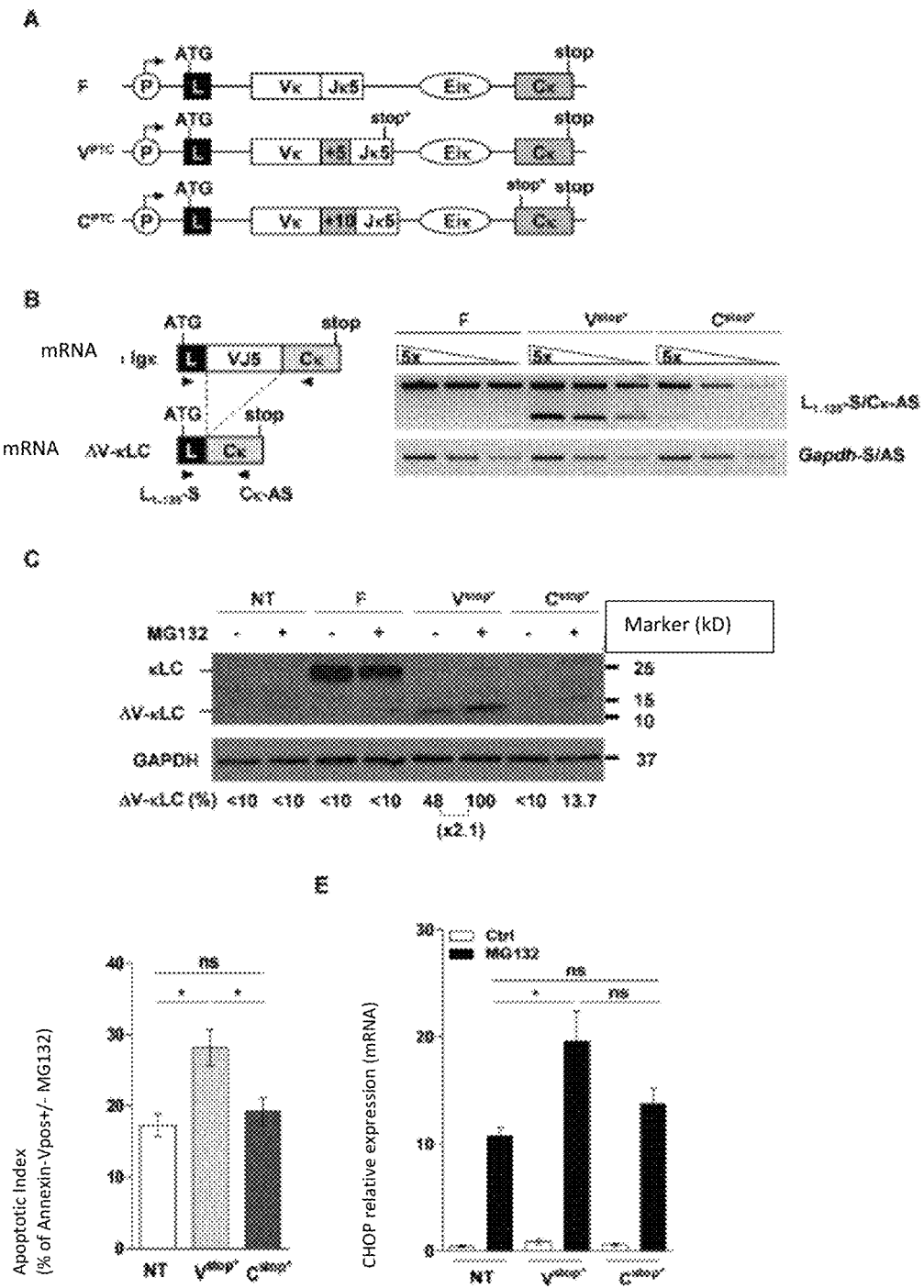

8 Claims, 8 Drawing Sheets
Specification includes a Sequence Listing.

```
                           SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: synthetic

<400> SEQUENCE: 1
atggcctggd yyvydctvyt yct                                           23

<210> SEQ ID NO 2
<211> LENGTH: 19
<212> TYPE: DNA
<213> ORGANISM: Homo sapiens

<400> SEQUENCE: 2
ctcccgggta gaagtcact                                                19

<210> SEQ ID NO 3
<211> LENGTH: 19
<212> TYPE: DNA
<213> ORGANISM: mouse

<400> SEQUENCE: 3
tcggttacca ttggacaac                                                19

<210> SEQ ID NO 4
<211> LENGTH: 22
<212> TYPE: DNA
<213> ORGANISM: mouse

<400> SEQUENCE: 4
gcacctccag atggttaact gc                                            22

<210> SEQ ID NO 5
<211> LENGTH: 25
<212> TYPE: DNA
<213> ORGANISM: human

<400> SEQUENCE: 5
agaagagact cacgtaggac ggtca                                         25

<210> SEQ ID NO 6
<211> LENGTH: 50
<212> TYPE: DNA
<213> ORGANISM: human

<400> SEQUENCE: 6
gaaggagagg ggagaagaga ctcacgtagg acggtcacct tggtccctcc              50

<210> SEQ ID NO 7
<211> LENGTH: 50
<212> TYPE: DNA
<213> ORGANISM: human

<400> SEQUENCE: 7
ggagggacca aggtgaccgt cctacgtgag tctcttctcc cctctccttc              50
```

```
<210> SEQ ID NO 8
<211> LENGTH: 50
<212> TYPE: RNA
<213> ORGANISM: human

<400> SEQUENCE: 8
ggagggacca aggugaccgu ccuacgugag ucucuucucc ccucuccuuc            50
```

USE OF ANTISENSE OLIGONUCLEOTIDES FOR PRODUCING TRUNCATED IG BY EXON SKIPPING FOR THE TREATMENT OF DISEASES INVOLVING B CELLS

SEQUENCE LISTING SUBMISSION VIA EFS-WEB

A computer readable text file, entitled "045636-5433-SequenceListing.txt," created on or about Apr. 12, 2019 with a file size of about 7 kb contains the sequence listing for this application and is hereby incorporated by reference in its entirety.

The present invention relates to the treatment of diseases involving cells of B lineage, B cells or plasma cells. In particular, it relates to the use of antisense oligonucleotides (AON) capable of inducing an exon skipping in the variable or constant regions of the immunoglobulin heavy or light chains for the treatment of diseases involving B cells, as well as mixtures of such AONs. Finally, the invention relates to a method for raising awareness for the treatment with proteasome inhibitors in the treatment of multiple myeloma.

PRIOR ART

Multiple Myeloma

Multiple myeloma (MM) is an incurable cancer characterized by the presence in the bone marrow of a tumor clone of plasma cells. It accounts for about 1% of cancers and 10% of malignant hemopathies, making this neoplasia B the second cancer of hematopoietic origin after lymphoma (Kyle and Rajkumar, 2009). The incidence of MM presents a large variation ranging from 0.4 to 6.3 cases per 100,000 people. The risk of developing MM increases with age with a median age at diagnosis >65. The incidence of MM is also higher in men than in women. Persons exposed to high levels of radiation (ionizing radiation, nuclear radiation) and pesticides also appear to have higher risks of developing MM. In most MM patients, the disease begins with an asymptomatic stage called MGUS. (Monoclonal Gammopathy of Undetermined Significance), before progressing to myeloma (Landgren, 2013).

The clinical manifestations commonly seen in patients with MM are: hypercalcemia, renal failure, anemia and bone lesions. Other symptoms such as bone pain, great fatigability, recurrent infections and weight loss are frequently observed (Bird et al, 2011; Rajkumar, 2011). These clinical manifestations are caused by the abnormal production of a monoclonal Ig (historically called M protein) by the plasma cell clone.

Although MM remains an incurable disease, recent advances in cancerology and the emergence of new therapeutic agents have improved patient overall survival (Kumar et al, 2014).

The diagnosis of MM is based on the detection and evaluation of a monoclonal component (M protein) by electrophoresis and immunofixation on patients' serum and/or urine, characterization and quantification of Ig (for example: IgM, IgG, IgA, Igκ or Igλ light chains, "free" light chain levels, etc.). Bone marrow biopsies are performed to evaluate plasma cell infiltration as a marker of progression and aggressiveness of the disease. Bone lesions are evaluated by imaging (X-ray, NMR, tomography). The serum concentration of other biological factors (2-microglobulin, albumin, C-reactive protein, creatinine, hemoglobin, calcium, lactate dehydrogenase) makes it possible to classify the stage of the disease and to predict its evolution. The search for chromosomal abnormalities (translocation, deletion, hypo/hyperdiploidy) also allows to classify the risks of progression of the disease. Most of these criteria are used in the international classification systems of the MM: "International Staging System: ISS" (Greipp et al., 2005) and "The Mayo Stratification of Myeloma and Risk-Adapted Therapy: mSMART" (Mikhael et al., 2013).

Treatment of patients with myeloma often includes three steps:

An induction phase: intended to reduce the tumor mass before autologous stem cell transplant. This chemotherapy generally includes immunomodulatory agents (such as Thalidomide), proteasome inhibitors (such as Bortezomib marketed as Velcade®) and Dexamethasone.

A possible autologous stem cell transplant, performed in eligible patients who responded satisfactorily to the induction phase.

A maintenance phase: consisting of a combination of chemotherapy and immunomodulatory agents which may include alkylating agents and Lenalidomide. This treatment is maintained until the patients' relapse.

Different treatments can then be administered to relapsed patients (Dispenzieri et al., 2009).

The agents used in the treatment of MM are divided into 5 main classes: alkylating agents, anthracyclines, corticosteroids, immunomodulating agents and proteasome inhibitors.

The Humoral Immune Response

The humoral immune response first involves the membrane form of immunoglobulins (Ig) and then relies on the secretion of soluble Ig: the antibodies. Ig are heterodimeric proteins composed of 4 polypeptide chains including 2 identical light chains and 2 identical heavy chains joined together by a variable number of disulfide bridges. Ig have variable regions carrying antigenic specificity and constant regions which, for heavy chains, determine the effector function of the secreted antibodies. According to the structure of the constant regions, there are two types of light chains (kappa or lambda) and five major types of heavy chains ($\mu$, o, $\gamma$, £ or $\alpha$) defining the class of Ig. If they prove to be functional, the successive rearrangements of the genes encoding the variable regions (VJ for the light chains; DJ, then V(D)J for the heavy chains) form a variable exon that can be transcribed and spliced on the genes coding constant regions. At the level of the heavy chain locus, this exon is expressed first with the constant gene C$\mu$ located immediately downstream. Then, a second type of rearrangement called "class switching" or "isotypic switching" can intervene. It causes the deletion of the C$\mu$ gene and allows the expression of a new constant gene (for example C$\gamma$) with the same rearranged variable region. These multiple steps of recombination of Ig genes are finely regulated during the maturation of B cells, ranging from the stage of B-lymphoid progenitors to that of antibody secreting plasma cells.

Organization of Ig Genes

The genes encoding the different immunoglobulin chains occupy 3 loci located on separate chromosomes. They have a general common structure and are specifically expressed in the B cell line. Each is composed of multiple gene segments coding for the variable portion of the receptors for the antigen and one or more genes coding for the constant part. In their germinal arrangement, Ig heavy and light chain genes are not directly functional. To become fully functional, these genes must undergo internal modifications or intra-genic rearrangements. These rearrangements take place at the early stages of B ontogeny, between the segments coding for the variable part of the heavy and light chains and are called V(D)J recombinations.

Human locus of Ig heavy chains (chromosome 14): the heavy chain genes comprise a large number of V (variable) segments and D segments (these so-called "diversity" segments are specific to the heavy chain locus) and a group of 6 J segments; there are also 9 genes encoding constant regions. Each constant gene is composed of multiple exons encoding the structural domains specific to each heavy chain. During V(D)J recombinations, a segment is randomly associated with one of the 6 J segments, and the rearrangement of this D-JH association is carried out with a V segment. The variable part is associated with the constant region by splicing the messenger RNA. The passage of the membrane form to the secreted form of the Ig is carried out by alternative splicing of a same primary heavy chain transcript.

Kappa light chain locus (chromosome 2): the κ light chain genes comprise numerous V segments and 5 functional J segments; there is then a single Cκ constant gene. During rearrangements of the light chain genes, a V segment is randomly joined to one of the 5 J segments.

Lambda light chain locus (chromosome 22): The λ light chain genes have a relatively different architecture from the other two so-called grouped loci. There are many V segments (29-33) and 4-5 functional J and C segments.

Differentiation of B Cells into Plasma Cells

The origin of the plasmocytic clone is a post-center germinal B cell. The differentiation of B cells is carried out in two phases: an independent phase of the antigen in the bone marrow and a phase dependent on antigenic activation in secondary lymphoid organs (spleen, lymph nodes, etc.). During the independent phase of the antigen, B precursors undergo rearrangements of their Ig genes. These recombinations take place by an ordered assembly of the V (variable), D (diversity) and J (junction) segments for the Ig heavy chains and the V and J segments for the light chain loci. These V(D)J junctions are highly diversified and allow the expression of a multitude of Ig capable of recognizing an almost infinite number of antigens. Each B cell synthesizing a single Ig, usually devoid of reactivity to self-antigens, is selected positively. After different stages of proliferation, this B cell will give rise to clones expressing the same Ig.

Recognition of the antigen by surface immunoglobulin then results in the entry of activated B cells into germinal centers where several processes of genetic modification occur. Active B cells can notably undergo rearrangements at the level of the constant heavy chain genes. These genetic recombinations are influenced by many cytokines and allow the expression of new classes of immunoglobulins other than IgM. Class switching mechanisms are based on the joining of switch regions located on the 5' side of constant segments and the elimination of intervening regions in the form of extrachromosomal circular DNA. In germinal centers, somatic mutations, which correspond to specific nucleotide modifications or short insertions or deletions located essentially in the variable segments, allows the increase of the affinity of the B cell receptor for antigen and to constitute a pool of high affinity memory B cells. Activated B cells can also differentiate into plasma cells which synthesize and secrete in the serum very large amounts of immunoglobulins. Plasma cells can then reach the bone marrow where they receive survival signals such as interleukin-6 produced by stromal cells. These long-lived plasma cells may persist for several months or even years in the body. In agreement with their post-center germinal status, myeloma cells produce IgG and IgA, more rarely IgD and IgE, and have high somatic hypermutations rates in their immunoglobulin genes (Anderson and Carrasco, 2011).

Massive Ig synthesis by plasma cells needs to be finely regulated to avoid overloading the endoplasmic reticulum (ER), which is detrimental to plasma cell survival.

The inventors have now obtained innovative results highlighting the toxicity of truncated Ig during the physiological differentiation of plasma cells (Srour et al., J Exp Med, 2015, accepted publication). Interestingly, the production of truncated Ig by the plasma cells induces cell stress and causes apoptosis of these plasma cells.

Based on these results, the inventors have developed a novel therapeutic approach which involves inducing the production of truncated Ig to remove pathological plasmocytes using antisense oligonucleotides (AON). These AONs can cause exon skipping at the RNA of Ig heavy or light chains, resulting in the expression of truncated Ig.

DETAILED DESCRIPTION OF THE INVENTION

The present invention relates to a method for treating diseases involving B cells comprising administering to a patient at least one AON capable of inducing exon skipping in one of the variable or constant regions of one of the heavy or light chains of immunoglobulins.

"B cells" means B cells and plasma cells.

In a first embodiment, the present invention relates to the use of an AON for the elimination of the variable region of Ig light or heavy chains.

The results of the experimental part illustrate such an approach, particularly in Example 3. In particular, the inventors have shown that by transfecting a myeloid lineage with an AON capable of hybridizing specifically with the sequence of the splice donor site of the light chain exon VJ expressed by this clone, the cells produce truncated Ig which cause their death by apoptosis. This result constitutes the proof of concept of the present invention. The inventors have also validated a methodology for studying the efficacy of AON treatments in the absence of transfection. The present invention therefore relates to the use of an AON targeting the VJ variable portion of Ig light chains to eliminate a clone of the B line. Such an approach is illustrated in Example 4.1.

In a preferred embodiment, the invention consists in using an AON directed against the splice donor site of the variable exon located on the λ light chain. A preferred AON for this use is the AON of sequence SEQ ID NO.5.

Likewise, the present invention can be implemented using an AON capable of inducing exon skipping so that the Ig produced is devoid of the VDJ variable portion of the heavy chains. Such a strategy is illustrated in Example 4.2.2.

By "AON capable of inducing exon skipping" is meant any AON specifically binding to the target region so that the mature mRNA obtained after splicing does not allow translation of the protein domain that needs to be removed. By "domain to be eliminated" is meant either the variable region of a heavy or light chain, or at least a part of the constant region of a heavy chain. The sequence targeted by the AON may contain the splice donor site, the splice acceptor site, or splicing regulatory sequences, e.g. enhancer, located in the intronic or exonic regions. In addition, an AON according to the invention is capable of inducing an exon skipping by hybridizing with a sequence which comprises a splice donor site, a splice acceptor site or splicing regulatory sequences located in the intronic or exonic regions of variable or constant regions of immunoglobulin chains. This AON can be used in the treatment of diseases involving B cells.

The therapeutic approach aimed at causing the B cells to produce an Ig devoid of variable domain can be implemented within the framework of a personalized medicine. Once the B clone responsible for the disease has been identified, sequencing of the variable region is performed and an AON capable of hybridizing specifically to that sequence can be selected and administered as a drug.

For example, in the case of MM, the monoclonal Ig produced by the tumor clone (e.g., IgG, IgA, Igκ or Igλ light chains) is sought by electrophoresis and immunofixation on patients' serum. Bone marrow biopsies then allows the evaluation of the plasma cell infiltration, and to characterize the V(D)J rearrangements of the tumor clone by specific amplification of Ig transcripts (Van Dagen J J M et al, Leukemia 2003, Bridoux et al. Am J Kidney Dis 2005). After identification of the V(D)J rearrangements carried by the tumor clone, a specific AON of the targeted rearrangement is used to produce a truncated Ig devoid of a variable domain.

A similar preliminary approach, by amplification of Ig transcripts, is applicable to the characterization of V(D)J rearrangements of any tumor B cell.

Thus, generally, the type of Ig produced by the pathological clone can be determined from a blood sample or lymphoid tissue of the patient. It is then necessary to determine the type of the light or heavy chain of the clone involved. In addition, as part of a personalized medicine approach to the treatment of myeloid cancer, the specific variable sequence of the tumor clone can be obtained from a spinal biopsy of the patient. After identification of the V(D)J rearrangements carried by the Ig heavy and light chain genes of the tumor clone, the elimination of the variable exon is carried out by means of an AON directed, for example, against the splice donor site of the J segment involved in the rearrangement.

Thus, in the context of a personalized medicine approach, the use of an AON according to the invention comprises the following steps:
  a. Identification of the B cell clone responsible for the disease from a patient sample: identification of heavy and light chain isotypes of the monoclonal Ig produced by this clone;
  b. Characterization of the particular rearrangement of the variable region of heavy or light chains, expressed by said B cell clone;
  c. Providing at least one AON capable of inducing exon skipping in one of the variable regions of one of the immunoglobulin chains of said clone;
  d. Administration of said AON or AON mixture to the patient.

These therapeutic approaches of personalized medicine allowing the elimination of the variable domain are based on the identification of the V(D)J rearrangement of a tumor cell. These strategies therefore take into account eventual somatic mutations introduced on the variable exons during the Ig affinity maturation process.

Thus, a therapeutic approach consisting in the administration of an AON capable of inducing exon skipping in the variable region of the Ig light or heavy chains is particularly suitable in the context of the treatment of multiple myeloma, AL amyloidosis, non-Hodgkin's lymphomas, chronic lymphocytic leukemia, Waldenstrom's disease, and any other type of B cell cancer involving the production of a monoclonal Ig.

This personalized approach offers the advantage of allowing to specifically eliminate the tumor clone while sparing healthy B cells and thus preserving the patient's immune defenses. This targeted therapeutic approach therefore represents a major innovation, in contrast with the "heavy" therapies currently used in B cell cancers.

In a second embodiment, the present invention relates to the use of an AON for the elimination of at least one exon from the constant region of Ig heavy chains to treat diseases involving B cells.

The inventors have demonstrated that the production of a truncated Ig by a B cell causes a stress in the ER which leads to the death of said cell by apoptosis. Thus, one of the hypotheses explaining the toxicity of these truncated Ig is that the cell may be sensitive to the production of misfolded proteins (due to the absence of certain domains). In this context, it can be predicted that a B cell producing Ig devoid of at least part of their constant domain will present the same phenotype as a cell expressing Ig devoid of their variable domain.

Thus, in a particular embodiment, the invention relates to an AON capable of inducing an exon skipping in the constant region of the heavy chain to eliminate at least one of the CH1, CH2 or CH3 exons. The approach to produce Igs devoid of at least part of their constant domain is illustrated in Example 4.2.3.

This therapeutic strategy allowing the elimination of a constant exon from Ig heavy chains has a broader spectrum of action than the previously described personalized medicine for the elimination of the variable domain, based on the identification of the V(D)J rearrangement of a tumor cell. Indeed, the elimination of a constant exon allows to specifically target B cells expressing either IgM, IgG, IgA or IgE.

To differentiate it from the "personalized medicine" approach, the term "generic medicine" will be used to describe the approach that treats a pathology according to criteria independent of rearrangements of variable regions. The choice of region to be targeted will then depend on isotypes of Ig heavy or light chains produced by pathological B cells.

This generic strategy is applicable for the treatment of cancers of the B cell lymphoid lineage (as an alternative to the approach of personalized medicine defined above), but also for treating a large number of pathologies involving non-cancerous B cells.

Thus, in a particular embodiment, the present invention involves the use of AON drugs targeting Ig heavy chain constant genes; this therapeutic approach could be applied to many pathologies such as:
  immediate allergy by targeting B cells producing IgEs,
  immunological pathologies involving IgAs,
  certain immuno-allergic pathologies involving deposits of IgAs (IgA nephropathy, rheumatoid purpura, etc.) or immunopathological properties specific to IgAs (dermatitis herpetiformis, cutaneous diseases with linear deposits of IgAs, etc.) by targeting B cells producing IgAs,
  autoimmune diseases involving autoantibodies and/or tissue-specific antibodies by targeting the cells producing a class of autoantibodies having demonstrated direct pathogenicity (e.g. autoimmune thyroiditis, Biermer's disease, autoimmune cytopenia, etc.),
  pathologies related to tissue deposits (renal, cardiac, hepatic, etc.) of monoclonal immunoglobulin chains (amylase, Fanconi syndrome, Randall syndrome, cryoglobulinemia, etc.), in transplantation (acute rejection involving IgG-class alloantibodies).

Another subject of the present invention is an AON capable of inducing exon skipping in the RNA of immunoglobulin heavy or light chains, for its use in the treatment of diseases involving B cells. Thus, an AON according to the invention is capable of inducing the production of an immunoglobulin devoid of variable region on heavy or light chains, or at least a portion of its constant region on heavy chains, for its use in the treatment of diseases involving B cells.

The present invention also relates to the use of an AON capable of inducing the production of an immunoglobulin devoid of variable region on heavy or light chains, or at least a portion of its constant region on heavy chains, for the preparation of a drug intended for the treatment of diseases involving B cells.

In view of the foregoing, the therapeutic applications of AONs targeting Ig transcripts to induce exon skipping and truncated Ig production can cover almost all diseases affecting B cells.

In the context of a generic approach such as that defined above, the present invention can be implemented by proposing mixtures of AON as drugs.

Thus, another object of the present invention is an AON mixture capable of specifically inducing the production of a truncated Ig.

AON mixtures can be provided to broaden the spectrum of action and/or increase the toxicity of these therapeutic approaches. The combinations are multiple, hereinafter is a presentation of some mixtures presenting a great therapeutic interest and/or a high potential as "industrializable" generic drugs.

AON mixture targeting the J segments involved in the V(D)J rearrangements of heavy and light chains of a B clone.

Such a mixture would be particularly interesting in the context of a personalized medicine approach to increase treatment toxicity, thus its effectiveness.

AON mixture targeting all J segments of kappa light chains

Such a mixture would allow to selectively destroy the Igκ population which represents approximately 60% of the B cells. The advantage of such a generic approach is that it allows to eliminate the tumor clone while preserving the B cells expressing Igλ (about 40% of the total B population). It is useful for treating diseases in which the incriminated Ig is an Igκ.

AON mixture targeting all J segments of lambda light chains

Such a mixture would allow to selectively destroy the Igλ population which represents about 40% of the B cells. The advantage of such a generic approach is that it allows the elimination of the tumor clone while preserving the B cells expressing Igκ (about 60% of the total B population). It is useful for treating diseases in which the incriminated Ig is an Igλ.

AON blend targeting all J segments of heavy chains

Such an approach would allow the destruction of all the B cells, that is to say to achieve immunosuppression.

Thus, it should be noted that in the context of the invention, the term "an AON" may be replaced by "an AON mixture" without this affecting the uses and methods described.

The choice of the AON for targeting the sequences previously described is within the reach of those skilled in the art. Such AONs can be obtained from commercial companies specializing in the preparation of AON on demand.

The present invention also relates to a method of sensitization for the treatment of MM by way of proteasome inhibitors, comprising administering an AON capable of inducing the production of an immunoglobulin devoid of variable region on heavy or light chains, or at least a portion of its constant region on the heavy chains, within the B clone responsible for MM.

The invention also relates to an AON capable of inducing the production of an immunoglobulin devoid of variable region on heavy or light chains, or a portion of its constant region on the heavy chains, for its use in the treatment of multiple myeloma in combination with an inhibitor of the proteasome pathway.

The treatment of choice for MM is currently Bortezomib (Bz), a proteasome inhibitor. However, this treatment has significant side effects and some patients are or are becoming resistant to it.

It should be noted that the joint use of an inhibitor of hsp90 and Bortezomib (Bz) has synergistic effects, respectively causing an increase in the rate of misfolded proteins and a decrease in their degradation by the proteasome (Richardson D G and al., Br J Haematol 2011). Therefore, therapeutic protocols aimed at increasing cell stress to sensitize cells to Bz treatment therefore seem very promising, and particularly suitable for patients resistant to Bz. These combination therapies could also be used to treat MM patients with lower doses of Bz or space treatment periods. By "combined treatment" is meant concomitant administration of the proteasome inhibitor and AON or an AON mixture according to the invention, or the sequential administration of these drugs.

In this context, the inventors propose to use the therapeutic approach based on the use of AON as described in the present invention in combination with Bz treatment in patients with MM.

This combined approach can be performed with Bz but also with any other proteasome inhibitor.

Among the other proteasome inhibitors that could be used in combination with an AON or an AON mixture according to the invention, mention may be made of carfilzomib (Kyprolis™), and other molecules currently in development such as marizomib, ixazomib (MLN-978), delanzomib (CEP-18770) and ONX-912.

The advantages of the present invention emerge from the description of these embodiments and its applications. In particular, the proposed therapeutic approaches are non-invasive and allow precise targeting of the B cell population to be destroyed. Thus, side effects should be limited. In addition, the efficacy can be modulated by administering AON mixtures. These characteristics make this approach very attractive compared to current treatments which patients generally do not tolerate well and which are therapeutically unsatisfactory.

The AONs useful in the context of the present invention may be administered in any suitable galenic form. Currently, many therapeutic approaches using AONs are undergoing preclinical and/or clinical trials (Moreno and Pego, 2014).

The examples which follow are intended to illustrate certain embodiments of the invention and should not be considered as limiting its scope.

LEGENDS OF FIGS.

FIG. 1: Demonstration of exon skipping and analysis of the impact of truncated Ig in mouse B cells. A) Constructs used for transfection of mouse B cells (S194, Sp2/0). The different constructs allow the expression of transcripts of functional (F) or non-functional ($V^{stop*}$, $C^{stop*}$) Igκ light chains. B) RT-PCR analysis of the expression of Igκ messenger RNAs, normal or devoid of the variable exon ("ΔV-κLC: V domain-less κ light chains"). C) Protein analysis (Western Blot mouse anti-Igκ) of normal Igκ light chains (κLC: ~25 KD) and truncated (ΔV-κLC: ~12 KD) carried out on SP2/0 cells, transfected or not (NT), with or without treatment with a proteasome inhibitor (MG132: 1 µM, 8 h). D) Apoptotic index of S194 cells representing the increase of positive S194 Annexin V cells (%) after treatment with MG132 (1 µM, 5 hours). E) The relative expression of CHOP was analyzed by quantitative PCR on S194 cells treated or not with MG132 (1 µM, 5 hours). "Stop*: premature stop codon consecutive to an offset of the open reading frame at the junction of V and J segments."

Figure 2:
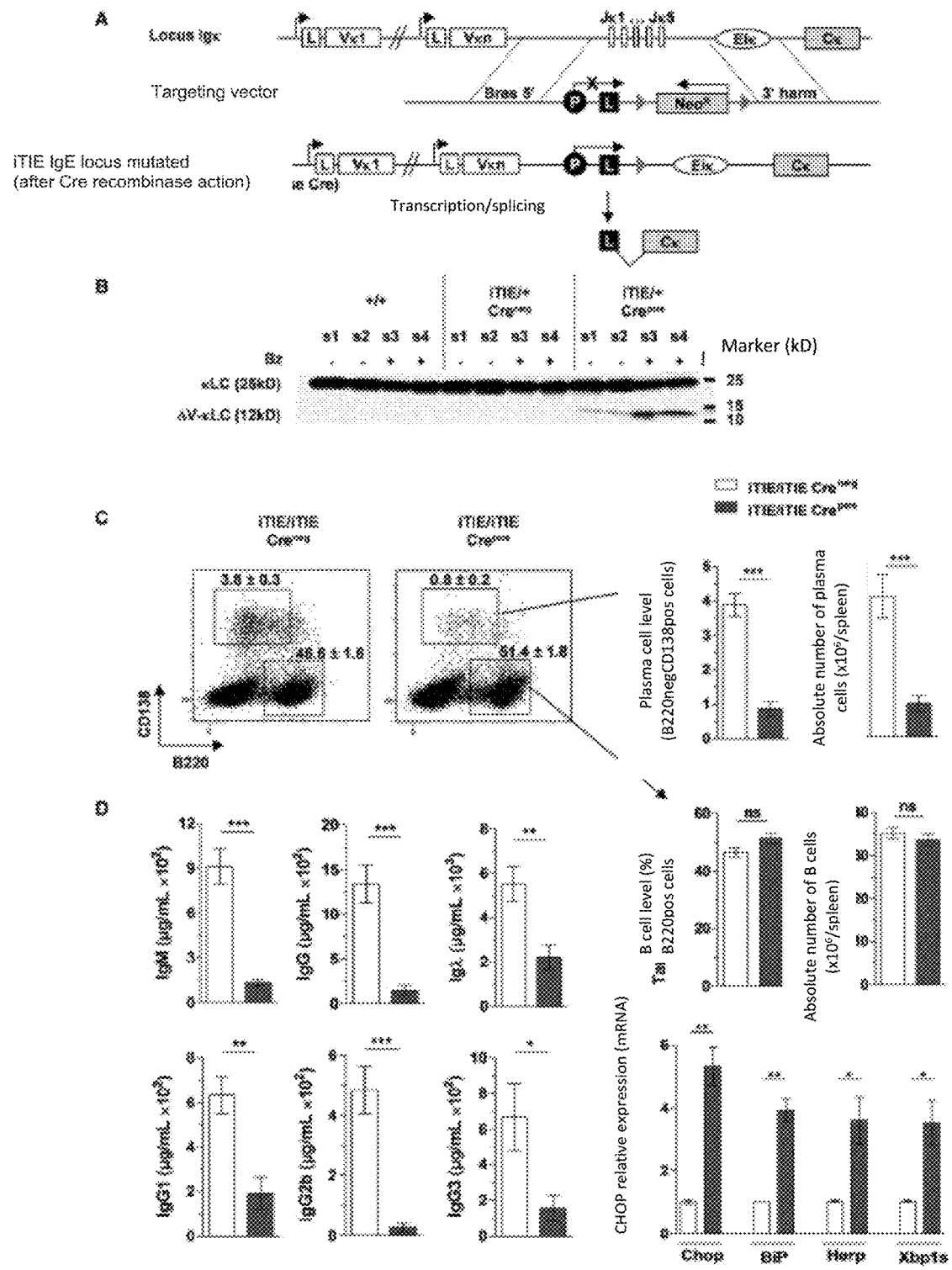

FIG. 2: Generation and analysis of the mouse model iTIE ("inducible Truncated-Ig expression") allowing the inducible expression of a truncated Ig. A) Representative Diagram of the model allowing to produce a truncated Ig (L: leader exon; Cκ: Cκ constant exon). The iTIE/+ animals were crossed with mice expressing the Cre recombinase to eliminate the NeoR gene and allow the expression of L-Cκ short transcripts without variable exon. B) Demonstration of truncated Ig ("ΔV-κLC: V domain-less κ light chains") only in mice expressing Cre recombinase ($Cre^{pos}$). Protein analysis (Western Blot mouse anti-Igκ) of normal Igκ light chains (κLC: ~25 KD) and truncated (ΔV-κLC: ~12 KD) by Western Blot (mouse anti-Igκ). The administration of Bortezomib (Bz) was performed intraperitoneally in the iTIE mice as indicated in the "Methods" section. C) Flow cytometric analysis of B cell populations ($B220^{pos}$) and plasma cells ($B220^{neg}$ $CD138^{pos}$), carried out on spleen cells of homozygous animals iTIE/iTIE, expressing or not Cre recombinase, 7 days after immunization by sheep red blood cells. D) Analysis of Ig levels achieved on serum of mice aged 8 to 12 weeks, performed by ELISA as indicated in the "Methods" section. E) The plasma cells were sorted as indicated in panel C and transcript analysis was performed by quantitative PCR after normalization against GAPDH expression.

Figure 3:
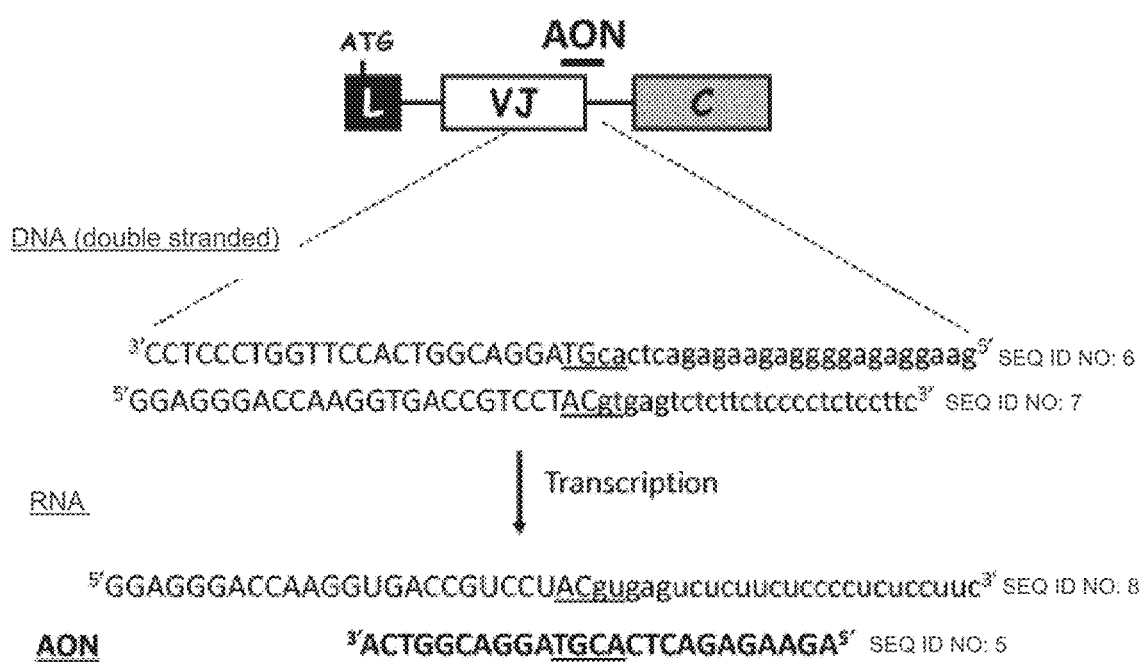

FIG. 3: Development of an AON targeting the splice donor site of the Jλ2 segment. Diagram representing the DNA sequence of the Igλ transcripts identified in the RPM18226 lineage (upper case: the sequence of the Jλ2 segment; in lower case: the intronic sequence located in 3' of Jλ2). An AON (in bold) capable of hybridizing to the primary transcripts at the splice donor site of the Jλ2 segment (underlined sequence) was synthesized. (L: "leader" exon; VJ: variable exon; C: constant exon). The sequence of this AON corresponds to SEQ ID NO.5.

Figure 4:
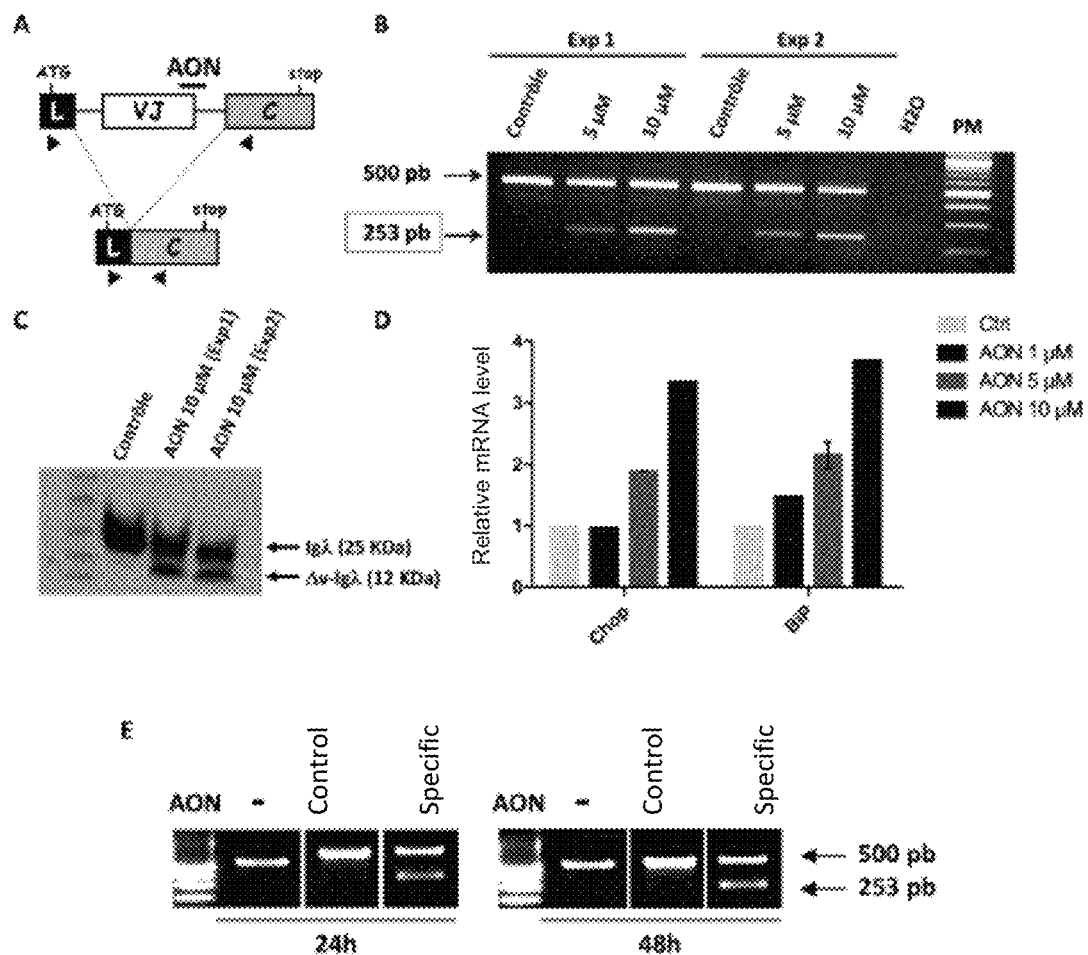

FIG. 4: Administration of an AON in RPM18226 myeloma cells. A) Diagram representing the administration of an AON capable of hybridizing to the primary Igλ transcripts, by targeting the splice donor site of the Jλ2 segment. The morpholino-type AONs (control and Jλ2 specific) were synthesized by Gene Tools, LLC. The position of the PCR primers is symbolized by arrows. (L: "leader" exon; VJ: variable exon; C: constant exon). B-D) The experiments were performed 48 hours after the transfection of RPM18226 cells ($3\times10^6$) by the AON. RT-PCR (B) and Western Blot protein analysis (C, anti-hIgλ) showing the exon variable elimination by exon skipping. D) Quantitative PCR analysis of normalized CHOP and BiP transcripts normalized against GAPDH expression. E) Elimination of the variable exon by passive administration of AON, in the absence of transfection. The RPM18226 cells ($1\times10^6$) were incubated for 4 hours with "vivo-morpholino" (control and Jλ2 specific) AONs (10 µM) marketed by Gene Tools, LLC. After washing, the cells are cultured for 48 hours and the exon skipping analysis is performed by RT-PCR after 24 hours and 48 hours of culture. The elimination of the variable exon is visualized by the appearance of a 253 bp band as indicated in Panel B.

Figure 5:
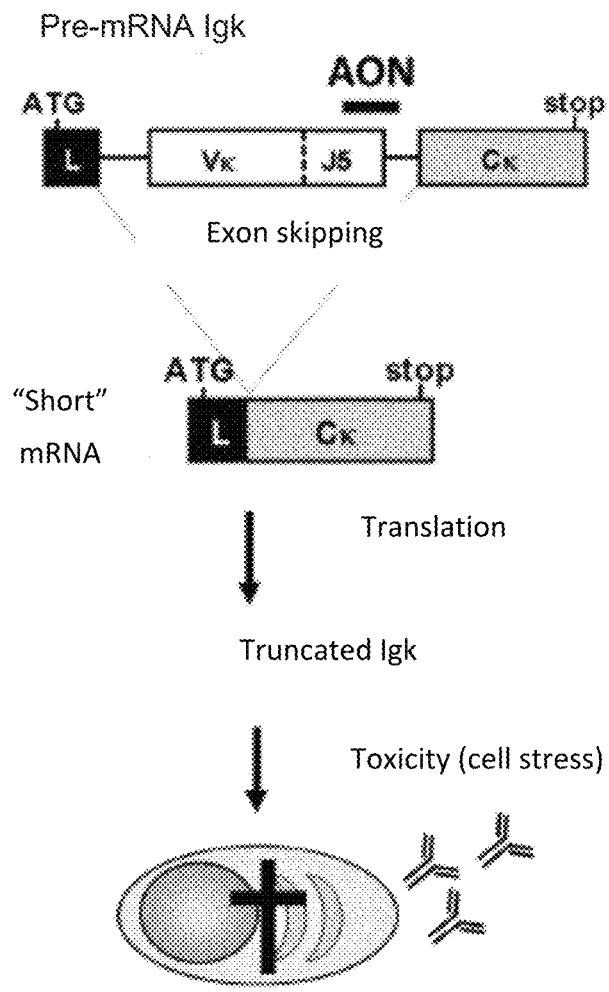

FIG. 5: Forcing exon skipping to produce toxic truncated Ig in plasma cells.

Diagram depicting the administration of an antisense oligonucleotide (AON) targeting the splice donor site of the Jκ5 segment. Hybridization of the AON on the primary Igκ transcripts causes the elimination of the VJ variable exon during splicing. The short transcripts allow the massive synthesis of an Ig chain devoid of toxic variable domain in the B-lymphoid lineage.

Figure 6:
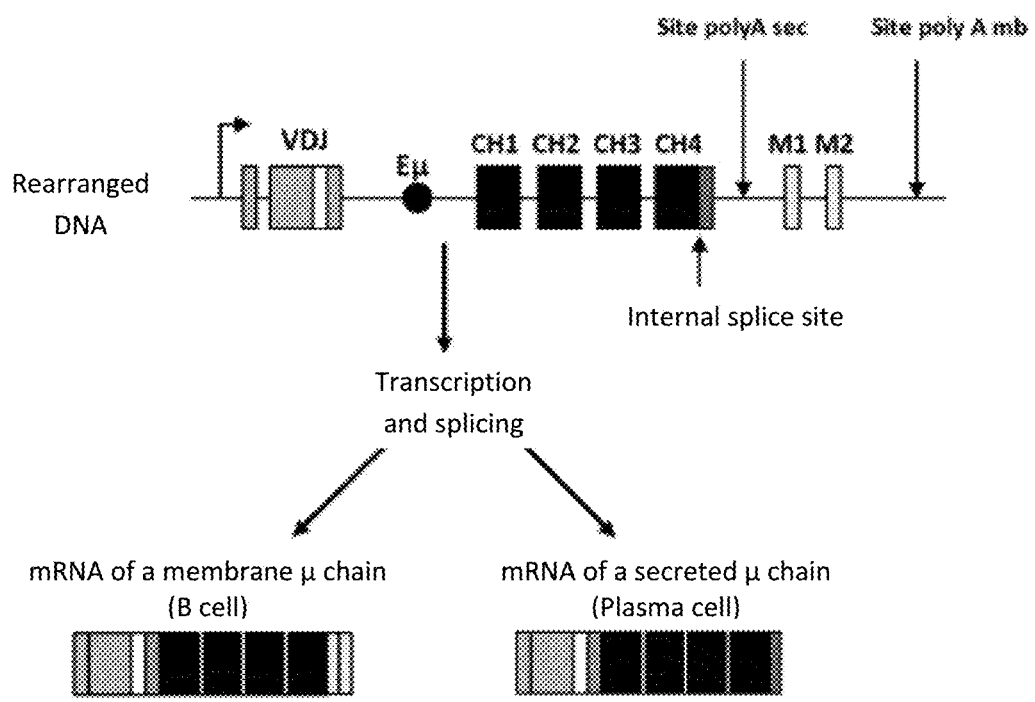

FIG. 6: Expression of a µ heavy chain and passage of the membrane form to the secreted form. In B cells and plasma cells, the Ig (here a µ heavy chain) are respectively produced in membrane and secreted form. Membrane Igs are produced by use of the CH4 internal splice site which is spliced on the first membrane exon (M1), the polyadenylation (polyA) site used being located after the second membrane exon (M2). Plasma cells produce essentially Igs in secreted form. In the case of a secreted p heavy chain, the CH4 internal splice site is not used, the transcript thus comprises the 3' part of this exon (represented in yellow) and uses the polyA site located directly downstream (adapted from Lefranc et al., 1999).

Figure 7:
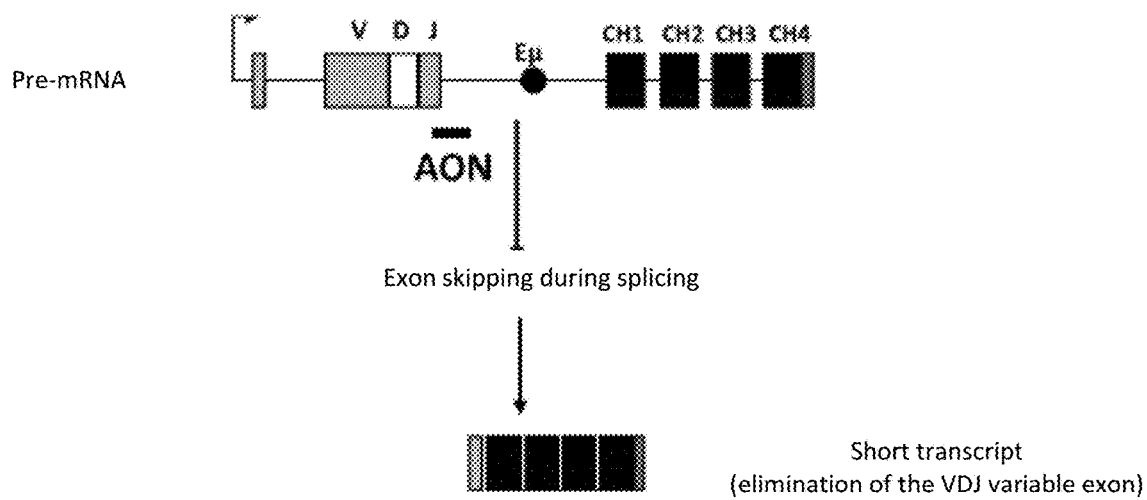

FIG. 7: Forcing the exon skipping to produce truncated heavy chains devoid of V domain. Diagram representing the administration of an antisense oligonucleotide (AON) targeting the J-segment splice donor site. Hybridization of the AON on primary transcripts causes the elimination of the VDJ variable exon during splicing. The short transcripts allow the massive synthesis of an Ig chain devoid of variable domain.

Figure 8:
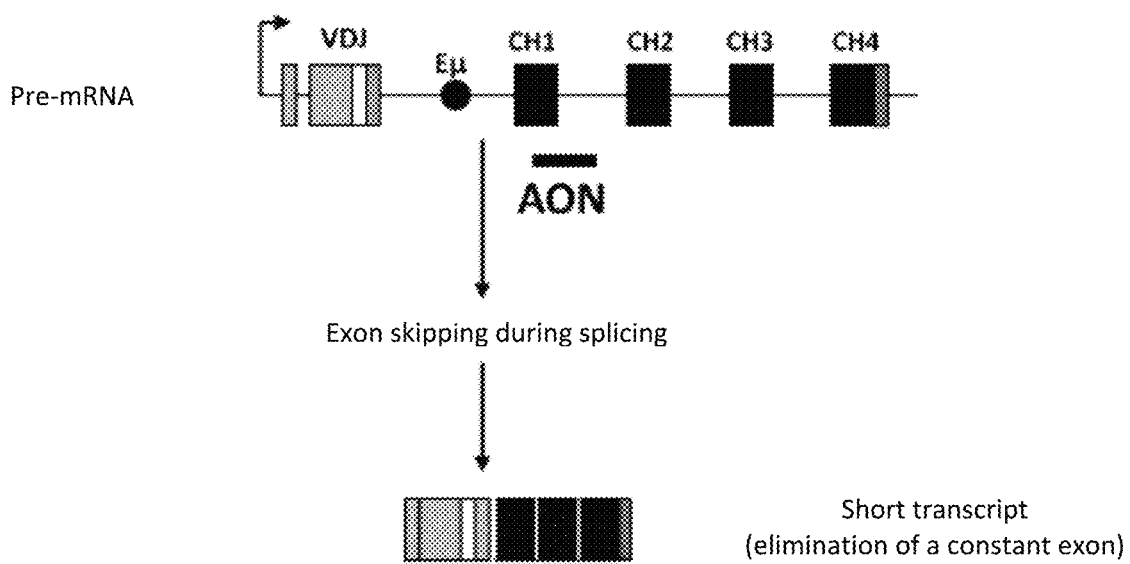

FIG. 8: Forcing the exon skipping to produce truncated heavy chains at a constant domain exon. Diagram representing the administration of an antisense oligonucleotide (AON) targeting the splice donor site of a constant exon (CH1). Hybridization of the AON on the primary transcripts causes the elimination of the constant exon (CH1) during splicing. The short transcripts allow the massive synthesis of an Ig chain devoid of one of the constant domains (CH1).

MATERIALS AND METHODS

Obtaining and Analyzing Transgenic iTIE Mice

The inducible truncated-Ig expression (iTIE) mouse model exhibits genetic modification at the Igκ light chain locus, obtained by homologous recombination as previously described (Sirac et al., 2006). The mouse Jκ segments were replaced by a cassette containing a promoter (pVH), a leader exon (L1-33) and a neomycin resistance gene (NeoR) surrounded by loxP sites. The transcription of the NeoR gene, in opposite orientation, allows to block the transcription and/or the splicing of the leader exon (FIG. 2A).

2-3-month-old mice were used in all experiments, carried out in accordance with the Ethical Committee Guidelines for Limousin Animal Experimentation (registered by the National Committee under number C2EA-33) and approved as part of the protocol registered under number CREEAL Jun. 7, 2012. The heterozygous mutant mice (iTIE/+) were crossed with C57BL/6 (B6) mice for at least 3 generations, and then crossed with Cre expressing mice to induce deletion of the NeoR cassette. B6 CMV-Cre mice are from the Mouse Clinic (Illkirch, France).

To analyze the late development of B cells, the cells were isolated from iTIE mouse spleen 7 days after immunization by intraperitoneal injection (200 µl/mouse) of sheep red blood cells (GR, BioMerieux® SA-France). In FIG. 2B, the mice received additional injections of Bortezomib (Sillag) subcutaneously (0.5 mg/kg) on days 5 and 6. The analysis of the B cells and plasma cells was carried out by flow cytometry, after labeling with anti-GL7, anti-B220 and anti-CD138 antibodies (BD Biosciences).

Cell Transfection and Passive Administration of AON

The murine lines (A20, S194 and Sp2/0) were cultured ($10^6$ cells/mL) in RPMI medium supplemented with 10% fetal calf serum (Invitrogen), sodium pyruvate, non-essential amino acids, β-mercaptoethanol, 100 U/mL penicillin and 100 µg/mL streptomycin (Gibco). The cells ($2 \times 10^6$) were stably transfected by electroporation according to the manufacturers (Amaxa) instructions. The VκJκS rearrangements are created by joining the segments $V\kappa_{1.135}$ and Jκ5. During the junction, nucleotides are integrated to create an offset of the reading frame mimicking non-functional rearrangements. Transfections were performed using a plasmid construct respecting the reading frame (F) and the non-productive $V^{PTC}$ and $C^{PTC}$ constructs, either separately or in an equimolar mixture of F and $V^{PTC}$ or $C^{PTC}$ as previously described (Chemin et al., 2010). The transfected cells ($1 \times 10^6$/mL) were treated with a proteasome inhibitor, MG132 (Sigma-Aldrich) (1 µM).

The myeloma cells ($3 \times 10^6$) (RPM18226 lineage) were transfected with different concentrations of antisense oligonucleotide (1, 5 or 10 µM AON-Jλ2: 5'AGAAGAGACT-CACGTAGGACGGTCA (SEQ ID NO.5), Gene Tools, LLC), by electroporation according to the manufacturers instructions (Amaxa). The analyzes were then performed 24 and 48 hours after transfection.

Passive administration of AON was performed with "vivo-morpholino" (control and Jλ2 specific) AONs, marketed by Gene Tools, LLC. These AONs have chemical modifications that give them the ability to passively enter cells. The development of this methodology applicable to patient cells represents a major advance for the realization of preclinical studies. The RPM18226 cells ($1 \times 10^6$) were incubated with AONs (10 µM in PBS) for 4 hours. After washing, the cells are cultured in complete medium and the exon skipping analysis is carried out by RT-PCR after 24 hours and 48 hours of culture.

Passive administration experiments of "vivo-morpholino" type AON were also performed on mouse primary B cells stimulated in vitro by LPS.

Protein Analysis

For Western Blot analysis, 4-20% polyacrylamide gels (Bio-Rad) were used. Each sample was then denatured at 94° C. for 3 minutes before loading. The gels were transferred to polyvinylidene fluoride (Bio-Rad) membranes with a Transblot® Turbo™ device. Membrane blocking was performed in PBST buffer (137 mM NaCl, 2.7 mM KCl, 1 mM Na2HPO4, 2 mM KH2PO4, 0.1% Tween® 20, pH 7.4) containing 5% skimmed milk powder. The signal was measured by chemiluminescence (ECL plus, GE Healthcare). Rabbit antibodies directed against the mouse HERP proteins (Santa Cruz Biotechnology), CHOP, BiP, IRE1α (Cell Signaling Technology), goat anti-Igκ (Beckman Coulter) and mouse anti-GAPDH (R&D Systems). The GAPDH signal strength was used for normalization between samples.

ELISA assays for determining Ig levels were performed from serum or culture supernatants, using sheep antibodies directed against mouse Ig (IgM, IgG1, IgG3, IgG2b, Igκ, Igλ and total IgG) (Southern Biotechnology) as previously indicated (Pinaud et al., 2001, Sirac et al., 2006). After addition of p-nitrophenyl phosphate (Sigma-Aldrich) to allow enzymatic revelation, the plates were read at a wavelength of 405 nm.

PCR and RT-PCR

To analyze the VJ rearrangements, the amplifications were carried out using specific pairs of human Igλs (Sens Leader-consensus: 5'-ATGGCCTGGDYYVYDCTVY-TYCT (SEQ ID NO.1), with D=A or G or T, Y=C or T, V=A or C or G, and CA-AS antisense: 5'-CTCCCGGGTA-GAAGTCACT (SEQ ID NO.2)), or specific to mouse Igκ ($L_{1.135}$-S: 5'-TCGGTTACCATTGGACAAC (SEQ ID NO.3) and Cκ-AS: 5'-GCACCTCCAGATGGTTAACTGC (SEQ ID NO.4)). After cloning the amplification products into the pCR2.1-TOPO vector (Invitrogen) and sequencing, the VJ junctions were analyzed using the V-QUEST software (The international ImMunoGeneTics information System®).

Quantitative PCRs were performed on an ABI PRISM 7000 device using Taqman primers and probes specific for each gene, marketed by Life Technologies. The relative number of different transcripts was determined by the standard $2^{-\Delta\Delta Ct}$ method after standardization on GAPDH expression.

Statistical Analysis

The mean and standard deviation of the mean are represented. Statistical analysis of differences between values was calculated using a Student test using Prism GraphPad software (San Diego, Calif.).

RESULTS

Example 1: Impact of Truncated Ig Expression in Normal Plasmocytes 1.1 In Vitro Production of Truncated Ig In order to analyze the conditions of the exon skipping, mouse B cell lineages (S194 and Sp2/0) were transfected with constructs allowing the expression of different types of Igκ light chain transcripts (FIG. 1A):
functional Igκ transcripts with VJ rearrangement in phase
non-functional Igκ transcripts with nonsense codons, either at the 3' end of the VJ exon ($V^{stop*}$ construct), or in the C exon ($C^{stop*}$), derived from an offset of the reading frame during the junction of the V and J segments.

The analysis at the transcriptional level (FIG. 1B) and protein level (FIG. 1C) shows that the deletion of the V region, following a "skipping" of the VJ exon during splicing, is effective mainly when the V exon itself contains a nonsense codon (construction $V^{stop*}$).

It is known that the survival of plasma cells depends on their ability to withstand the stress response at the ER level associated with massive Ig synthesis (Cenci et al., 2011). As a result, the inventors have sought to ascertain whether the production of truncated Ig, i.e. with abnormal structures and folds, could impact plasma cell survival. To this end, they analyzed the apoptotic index with regard to the abundance of truncated Igκ chains ("ΔV-κLCs: V-domain less κ light chains"). They thus showed that the cells expressing the $V^{PTC}$ construct have a level of apoptosis greater than that of the non-transfected (NT) cells or expressing the $C^{stop*}$ construct (FIG. 1D). In addition, quantification of CHOP mRNAs (C/EBP homologous protein), a transcription factor implicated in ER-induced stress apoptosis (FIG. 1E), reveals an increase in the expression of this mRNA by more than a factor of 2 in relation to the amount present in the non-transfected cells. Therefore, the presence of ΔV-κLCs seems to cause an increase in ER stress that sensitizes plasma cells to CHOP-dependent apoptosis.

1.2 Production of Truncated Ig in an iTIE Mouse Model

In order to study the impact of truncated Ig production on B cell development and humoral response, an animal model with a genetic modification at the Igκ light chain locus was used. It allows to induce by design the synthesis of truncated Igs. The strategy used to construct this iTIE (inducible truncated-Ig expression) animal model is shown in FIG. 2A. Activation of the transcription of the modified Igκ locus using a Cre recombinase allows the expression of a mRNA devoid of the V region (FIG. 2A) as well as that of a corresponding truncated protein (FIG. 2B). This model has allowed showing that the expression of truncated Ig (ΔV-κLCs) affects the survival of normal plasma cells (FIG. 2C) and the humoral response (FIG. 2D). Crossbreeding of the iTIE model with DH-LMP2A mice were also carried out in order to generate B cells and plasma cells expressing only truncated Igκ chains (Casola S et al., Nat Immunol 2004, Bonaud A et al., Blood 2015). This new model allowed showing that the simple expression of truncated Igκ is sufficient to cause stress in the plasma cells and increase the expression of CHOP, BiP, IRE1a and HERP proteins (results not shown), thus revealing the intrinsic toxicity of Igκ chains devoid of V domain. This toxicity may be associated with the expression of stress markers present in the ER, in particular CHOP, BiP, HERP and Xbp1s, as shown in FIG. 2E. These in vivo results confirm that the expression of truncated Ig causes ER stress which leads to plasma cell apoptosis.

Example 2: Increased Sensitivity of Plasma Cell Lines Expressing Truncated Ig to Bz Treatment Studies conducted by Dr. Sirac's team demonstrated a high sensitivity to plasma cell Bz expressing a truncated Ig heavy chain (Bonaud et al., Blood, 2015).

The inventors have now shown that the presence of truncated Ig devoid of variable domain, encoded by short transcripts of Kappa light chains without variable exon, increases the apoptosis of plasma lineages treated with MG132, a proteasome inhibitor (FIG. 1C). Consistent with these results, the truncated Ig are actively degraded by the proteasome and their number increases significantly after Bz administration (intraperitoneally) in the iTIE mice (FIG. 2B).

Example 3: Feasibility Study of a Strategy by Exon Skipping to Increase the Synthesis of Truncated Ig in Tumor Plasmocytes In order to validate the concept of administration of AON to induce the production of truncated Igs, a cellular model was used. This experiment consisted in eliminating the VJ variable exon and forcing the synthesis of aberrant Igs in the myeloma lineage (RPMI 8226). This myeloma lineage expresses a Igλ. We amplified the Igλ transcripts using RT-PCR to identify the VJ rearrangement. After cloning and sequencing of the amplification product, the VJ rearrangement was analyzed on the IMGT site. The RPM1-8226 lineage expresses a VJλ2 rearrangement (IGLV2-14, IGLJ2). These cells were transfected with a "morpholino" type AON directed against the splice donor site of the Jλ2 segment (FIG. 4A) and commercialized by Gene Tools, LLC. A detailed representation of AON hybridization on the primary transcript is presented in FIG. 3 and the sequence of the AON used corresponds to the sequence SEQ ID NO.5. Interestingly, the AON effectively disrupts splicing and induces a large increase in short transcripts lacking the VJ variable exon (253 base pair band, FIG. 4B). In terms of proteins, the administration of AON induces the production of truncated Ig without variable domain (FIG. 4C). The AON-transfected cells showed high levels of the pro-apoptotic factor CHOP and the BiP chaperone protein, thus highlighting the cellular stress following the production of the aberrant Igs (FIG. 4D).

A study was also carried out in which the of the AONs are administered passively in the absence of transfection. RPM18226 cells were incubated with "vivo-morpholino" type AONs marketed by Gene Tools, LLC. These "vivo-morpholino" type AONs have chemical modifications that give them the ability to passively enter cells. As the results show (FIG. 4E), the exon skipping is significant after passive administration of "vivo-morpholino" type AON. An increase in exon skipping was also demonstrated after passive administration of "vivo-morpholino" type AON to primary mouse B cells, stimulated in vitro by LPS (results not shown). The validation of this methodology applicable to patient cells constitutes a major advance for the implementation of preclinical studies.

Example 4: Strategies for Obtaining Truncated Ig for Therapeutic Purposes 4.1 Supply of an AON Capable of Inducing an Exon Skipping Aimed at Producing Truncated Igκ or Igλ Light Chains without Variable Domain.

Ig light chain transcripts are composed of 3 exons: L ("leader"), VJ (variable) and C (constant).

In order to produce a truncated light chain devoid of variable domain, antisense oligonucleotides (AONs) targeting the VJ exon splice donor site can be used to eliminate VJ exons during splicing. From a mechanical point of view, the inventors have shown that plasma cells expressing these aberrant Ig die by apoptosis (Srour et al., J. Exp Med, publication accepted). This strategy is represented in FIG. 5.

4.2 Supply of an AON Capable of Inducing an Exon Skipping Aimed at Producing Truncated Heavy Chains.

The same strategy can be applied to the targeting of heavy chains. In this case, the AONs can target either the VDJ variable exon or the constant exons (CH1, CH2 or CH3).

4.2.1 Recall of the Mechanism of Production of μ Heavy Chains in B Cells and Plasma Cells.

The process of expression of μ heavy chains, either in membrane form in B cells, or in secreted form in plasma cells, is based on alternative splicing of mRNAs, as shown in FIG. 6.

4.2.2. Supply of an AON Capable of Inducing an Exon Skipping Aimed at Producing Truncated Heavy Chains, without Variable Domain.

The production of truncated Igs can also be induced by forcing the elimination of the variable domain of the heavy chains.

The elimination of the variable exons can be achieved by using an AON directed against the splice donor site of the J segment involved in the rearrangement, after identifying the VDJ rearrangement carried by the tumor clone. Thus, the mature mRNA does not contain a variable domain. This strategy is illustrated in FIG. 7.

4.2.3. Supply of an AON Capable of Inducing an Exon Skipping Aimed at Producing Truncated Heavy Chains, Devoid of One of the Constant Domains.

The production of truncated Ig can also be achieved by eliminating one of the constant domains of Ig heavy chains, as illustrated in FIG. 8.

The invention claimed is:

1. A method of treating a disease involving B cells in a human in need thereof comprising administering to the human an antisense oligonucleotide or antisense oligonucleotide mixture capable of inducing exon skipping at the RNA level of heavy or light chains of immunoglobulins.

2. The method according to claim 1, wherein the antisense oligonucleotide or antisense oligonucleotide mixture is capable of inducing exon skipping in the VJ variable region of the light chain or VDJ of the heavy chain.

3. The method according to claim 1, wherein the antisense oligonucleotide or antisense oligonucleotide mixture is capable of inducing exon skipping in the constant region of the heavy chain.

4. The method according to claim 1, wherein the antisense oligonucleotide or antisense oligonucleotide mixture is capable of inducing exon skipping by hybridizing with a sequence that comprises a splice donor site, a splice acceptor site, or splicing regulatory sequences located in the intronic or exonic regions of the variable or constant regions of the immunoglobulin chains.

5. The method according to claim 2, wherein the disease involving B cells is selected from multiple myeloma, AL amyloidosis, non-Hodgkin's lymphomas, chronic lymphocytic leukemia, Waldenstrom's disease and any other type of cancer affecting B cells and involving the production of a monoclonal Ig.

6. The method according to claim 3, wherein the disease involving B cells is selected from (i) immediate allergy by targeting IgE-producing B cells, (ii) immunological pathologies involving IgA, (iii) autoimmune diseases involving autoantibodies, (iv) pathologies related to tissue deposits of monoclonal immunoglobulin chains and (v) transplantation.

7. An antisense oligonucleotide mixture capable of inducing an exon skipping in the RNA of heavy or light chains of immunoglobulins.

8. A method of treating multiple myeloma in a human in need thereof comprising administering to the human an antisense oligonucleotide or antisense oligonucleotide mixture capable of inducing an exon skipping in the RNA of immunoglobulin heavy or light chains, in combination with an inhibitor of the proteasome pathway.

* * * * *